United States Patent [19]

Rhum et al.

[11] Patent Number: 5,019,350

[45] Date of Patent: May 28, 1991

[54] FLUORESCENT POLYMERS

[75] Inventors: David Rhum, Old Lyme; Richard S. Matthews, North Stonington, both of Conn.

[73] Assignee: Pfizer Hospital Products, Inc., New York, N.Y.

[21] Appl. No.: 829,350

[22] Filed: Feb. 13, 1986

[51] Int. Cl.$^5$ ............................................. G01N 21/64
[52] U.S. Cl. .............................. 422/82.07; 204/431; 204/433; 422/58; 422/68.1; 422/82.08
[58] Field of Search ................. 422/56, 57, 68, 86, 422/91, 58, 68.1, 82.07, 82.08; 436/172, 163, 165, 133, 136; 204/431, 433, 403

[56] References Cited

U.S. PATENT DOCUMENTS

| | | | |
|---|---|---|---|
| Re. 31,879 | 5/1985 | Lubbers et al. | |
| 3,544,484 | 12/1970 | Roth | 436/163 |
| 3,612,866 | 10/1971 | Stevens | |
| 3,904,373 | 9/1975 | Harper | |
| 4,003,707 | 1/1977 | Lubbers et al. | |
| 4,029,598 | 6/1977 | Neisius et al. | 422/56 X |
| 4,041,932 | 8/1977 | Fostick | |
| 4,194,877 | 3/1980 | Peterson | |
| 4,200,110 | 4/1980 | Peterson et al. | |
| 4,287,153 | 9/1981 | Towsend | 422/56 |
| 4,399,099 | 8/1983 | Buckles | 436/165 X |
| 4,476,870 | 10/1984 | Peterson et al. | |
| 4,548,907 | 10/1985 | Seitz et al. | 436/163 |
| 4,557,900 | 12/1985 | Heitzmann | 422/56 X |
| 4,558,014 | 12/1985 | Hirschfeld et al. | 422/56 X |
| 4,568,518 | 2/1986 | Wolfbeis et al. | 436/172 X |
| 4,587,101 | 5/1986 | Marsoner et al. | 436/172 X |

FOREIGN PATENT DOCUMENTS 2758036  7/1979  Fed. Rep. of Germany ...... 436/172

OTHER PUBLICATIONS

CRC Handbook of Chea & Physics D106-107, 1969-1970.
Raymond F. Chen, "Fluorescent pH Indicator", (1968), Analytical Letters, 1(7), 423-428.

*Primary Examiner*—Robert J. Warden
*Assistant Examiner*—Timothy M. McMahon
*Attorney, Agent, or Firm*—Peter C. Richardson; Lawrence C. Akers; Mark Dryer

[57] ABSTRACT

A sensor for the determination of the concentration of a dissolved substance in an aqueous medium comprising an optical fiber having on the distal end thereof an adherent, water-insoluble organic polymer having a plurality of fluorescent organic substituents, which may be the same or different, covalently bonded to said polymer through ester or amide linkages.

20 Claims, No Drawings

FLUORESCENT POLYMERS

BACKGROUND OF THE INVENTION

This invention relates to fluorescent polymers which are useful as water-insoluble indicators for the determination of the concentration of dissolved substances in an aqueous medium. The invention is also concerned with sensors comprising said fluorescent polymer indicators bonded to optical fibers.

The measurement in blood of pH levels and concentration of gases, particularly oxygen and carbon dioxide, is important during surgical procedures, post-operatively, and during hospitalization under intensive care and numerous devices for the measurement and display of said physiological parameters have been suggested in the art.

U.S. Pat. No. 4,003,707, Lubbers et al., and its reissue patent Re 31879, disclose a method and an arrangement for measuring the concentration of gases and the pH value of a sample, e.g. blood, involving the use of a fluorescent indicator enveloped by or sealingly embedded in a selectively permeable diffusion membrane. This patent discloses the use of beta-methyl-umbelliferone as an indicating substance for the measurement of pH values and pyrenebutyric acid as an indicating substance for the measurement of oxygen concentration.

The use of beta-methyl-umbelliferone as a fluorescent pH indicator was previously disclosed in an article by Raymond F. Chen, Analytical Letters 1[7], 423-428 [1968].

The use of pyrenebutyric acid as a fluorescent indicator for the determination of the concentration of oxygen in the blood also was known before the Lubbers et al. patent, as disclosed in U.S. Pat. No. 4,041,932, Fostick. Fostick discloses a method whereby blood constituents are monitored by measuring the concentration of gases or fluids collected in an enclosed chamber sealingly attached to a skin "window" formed by removing the stratum corneum over a small area of the patient's skin. The measurements in the enclosed chamber are made, inter alia, by determining the difference in intensity of light emitted from a fluorescent indicator.

The use of a pH sensitive dye indicator in conjunction with a fiber optic pH probe is disclosed in U.S. Pat. No. 4,200,110, Peterson et al. In U.S. Pat. No. 4,476,870, Peterson et al. disclose a similar technique utilizing dye fluorescence oxygen quenching. In both Peterson et al. patents the relevant fluorescent dye indicator composition is enclosed within a selectively permeable membrane envelope.

An apparatus for measuring oxygen concentration based on oxygen quenching of molecular luminescence is disclosed in U.S. Pat. No. 3,612,866, Stevens.

A sensor adapted to function satisfactorily in a biological environment should possess at least four characteristics: sensitivity, short response time, stability and bio-inertness.

Sensitivity depends upon the quantum efficiency of the fluorescent indicator, the concentration of the indicator present in the sensor and availability of the indicator to the substance, i.e. ion or gas, it must sense. Thus a sufficient amount of indicator must be available to produce a meaningful fluorescent response. However, if indicator molecules are too close together there occurs a type of behavior which is frequently detrimental to the sensor performance; this behavior is known as eximer fluorescence. Therefore, for a given indication there is an optimum indicator concentration for maximum sensitivity.

A further problem which must be solved in the construction of a fluorescent sensor is the availability of the indicator to the environment to be sensed. If the subject ions or gas cannot reach the indicator molecules the indicator will not respond to the presence or absence of said ions or gas. This problem is clearly related to the permeability of the structure in which the indicator molecules are embedded.

Also related to said permeability is the question of response time. If the substance to be sensed (i.e. ions or gas) diffuses very slowly through the structure the response time of the sensor will be comparatively long which greatly reduces its usefulness.

A sensor for blood gas or blood pH should be capable of use over a period of many hours or days. Recalibration of a sensor which is used in vivo is clumsy and inefficient or even impossible. Thus, the stability of the sensor is a key factor in determining its utility. A common problem in existing fluorescent sensor design is the gradual loss of the indicator from the sensor. This not only reduces the sensitivity, thereby creating instability in the sensor's indication even at constant concentration of the substance being sensed but also releases a chemical indicator into the blood stream. A device which releases chemical substances into the blood stream can not be considered to be bio-inert. As used herein, the term "bioinertness" is defined to mean that characteristic of a device, i.e. a sensor, whereby any and all chemical substances which are part of the device are so securely bonded to the structure of the device that they are not released or leached away from the device under normal operating conditions.

In each of the above prior art disclosures the problem of leaching of the indicating substance from the sensor, which is inherent when small molecules are embedded in a polymer matrix, was addressed by enveloping or embedding the indicator in a selectively permeable membrane.

In practice, said problem manifests itself as a progressive loss of sensitivity of the sensor as the indicator is lost; this requires a continual re-calibration of the sensor.

The stated prior art arrangement does not completely solve the problem, since a portion of the indicating substance is still leached from the sensor. Thus, the problem of re-calibration still remains, and, moreover, the released indicator goes into the patients bloodstream.

Accordingly, there is a definite need in the art for a sensor which is more stable in the sense that the indicator is not leached or washed away therefrom upon contact with body fluids.

It has now been found that the desired stability may be achieved if the indicator is chemically bonded to an appropriate polymer so that the resulting chemical entity may be contacted directly with the aqueous medium under examination without loss of the indicating substance. At the same time the bonding of the indicator to the polymer does not result in any reduction of the rapid response characteristics possessed by the free indicating substance. U.S. Pat. No. 4,194,877, Peterson, which is a companion case to the above-mentioned U.S. Pat. No. 4,200,110, discloses a hydrophilic polymer composition of acrylamide and a dye material selected from the group consisting of phenol red, brilliant yellow and rosolic acid. However, it is clear from the chemical structure of these particular dyes that they do not possess the necessary reactive sites to chemically combine with a polymer to form a chemical entity comparable with the novel fluorescent polymers of the present invention.

U.S. Pat. No. 3,904,373, Harper, discloses an insolubilized bound indicator consisting of an organic indicator covalently coupled by means of an organo-functional silane coupling agent to an inorganic carrier, for example a glass.

SUMMARY OF THE INVENTION

In accordance with the present invention there is provided a sensor for the determination of the concentration of a dissolved substance in an aqueous medium comprising an optical fiber having a distal end to which is stably bonded an adherent, water-insoluble organic polymer having a plurality of fluorescent organic substituents, which may be the same or different, covalently bonded to said polymer through ester or amide linkages.

The invention also provides a stable, rapid response fluorescent polymeric indicator for the determination of the concentration of a dissolved substances in an aqueous medium, said indicator comprising an organic polymer having a plurality of fluorescent organic substituents, which may be the same or different, covalently bonded to said polymer through ester or amide linkages.

As used herein, the term "plurality of fluorescent organic substituents" means that said substituents may be the same, i.e. derived from a single fluorescent compound, or different, i.e., derived from two or more fluorescent compounds, each of which is sensitive to the presence of a substance whose concentration is to be measured. When different fluorescent compounds are employed, they are chosen so that the emission spectra do not overlap and the response signals are consequently analysable.

The polymers suitable for use in the invention are those with functionality depending from the polymer chain, wherein said functionality includes hydroxyl groups, carboxyl groups or amine groups; and fluorescent molecules suitable for use in the invention include those having, in addition to the desired fluorescent properties and indicating properties, functionality suitable for forming ester or amide linkages with said polymeric structure.

Preferably, said water-insoluble organic polymer contains pendant hydroxyl groups, a proportion of said groups being esterified with one or more fluorescent organic carboxylic acids.

It is important that the functionality used to form said ester or amide linkages is located sufficiently remote from the fluorescent portion of the indicator molecule so that it does not adversely affect the fluorescent indicating capability of the indicator molecule when the said ester or amide linkages are formed. Generally a spacing of at least two or three carbon atoms is appropriate.

In preparing a sensor according to the invention, the fluorescent polymeric indicator, in order to be readily applied to the optical fiber, should be soluble in a solvent. However, after it is bonded to the fiber, it must not be lost therefrom during use of the sensor.

When preparing a $pO_2$ sensor, for example, the fluorescent polymer may be made rather hydrophobic. Such hydrophobic polymers do not swell or dissolve in water to any great extent. Consequently, when applied to an optical fiber, no special crosslinking measures need be taken to prevent its loss therefrom.

However, in those cases were ion transport is required, i.e. in pH measurement, the fluorescent polymer should swell with water to that ion transportation between the solution being examined and the indicating moieties of the fluorescent polymer may take place.

Accordingly, steps must be taken to prevent the fluorescent polymer from dissolving in the medium in which the sensor is immersed or swelling to the point where the polymer is detached from the fiber. This is accomplished according to the invention by the use of a cross-linking agent.

Thus, when a hydrophilic fluorescent polymer is to be employed in the construction of the sensor, the water-insoluble organic polymer adherent to the distal end of the optical fiber should comprise (i) the novel organic polymer containing hydrophilic groups and chemically bonded fluorescent substituents, and (ii) a cross-linking agent which reacts with said polymer so that the combination of polymer and cross-linking agent is water-insoluble although still partially hydrophilic. The cross-linking agent also may enhance the adhesion of the polymer to the surface of the optical fiber so that said polymer remains adherent even after extended immersion in aqueous fluids.

In a preferred embodiment the polymer contains hydroxyl groups. One or more fluorescent indicators are chemically bound to the polymer chain via an ester bond formed from a hydroxyl group of the polymer chain and a carboxylic acid or carboxylic acid derivative, e.g. alkyl ester, that is structurally part of the fluorescent indicating moiety. A proportion of the hydroxyl groups of the base polymer is thus modified, leaving a proportion of free hydroxyl groups. The modified polymer is consequently still hydrophilic. The residual hydroxyl groups on the fluorescent indicator tagged polymer are utilized in part for chemically crosslinking and thereby rendering the indicator containing polymer insoluble. A crosslinking agent (and its ratio to the modified base polymer) is selected such that the insoluble cured mass remains hydrophilic and is bonded to the optical fiber. It is important for the sensing of ions that the hydrophilic character of the mass be retained after curing since that property leads to the polymer being swollen by water, and therefore permeable to the species being sensed. The substance, e.g. hydrogen ions, to be detected by the fluorescent moiety or moieties gains access to the entire mass of sensing polymer as a result of the permeation of the polymer with the solution in which it is immersed, giving rapid response time and reversibility to the sensor. Examples of crosslinking agents that are reactive with hydroxyl groups are glutaraldehyde and poly(acrylic acid). The crosslinking or curing reaction may be accomplished by heating as is commonly practiced, or ambient temperature active curing agents, e.g. diisocyanates, may be used. Other suitable curing agents are known to those skilled in the art and still others are illustrated hereinafter in Examples 7 and 8.

The sensor according to the invention may be used directly in contact with the aqueous medium under examination or it may be used in conjunction with a permeable membrane.

A sensor in accordance with the invention preferably is adapted to be used in conjunction with a light emitting and measuring apparatus to form a complete system for analysis of certain constituents of blood or other liquids as listed below. The sensor may be employed invasively, i.e., placed transdermally into a patient's vascular system and in contact with circulating blood, or non-invasively, i.e., in contact with blood external to a body, as in a heart-lung machine, or in a manually drawn sample of blood. The light-emitting and detecting portion of the analytical system is not part of this invention but is mentioned herein to indicate the complete concept and to indicate the importance of the improved features of the novel sensor, including stability, sensitivity, rapidity of response, and reversibility in the context of the entire working system. The light emitting and measuring device transmits a specific frequency or group of frequencies through the optical fiber to impinge distally on the fluorescent polymer. The frequency or frequencies are chosen to excite the indicator molecules in the polymer so that they fluoresce. The intensity of fluorescence of a given indicator is related directly to the concentration of the species to which the indicator is sensitive. Consequently a variably intense fluorescence will be emitted by the indicator according to the conditions in the solution being analyzed. The emitted fluorescent light is carried by the optical fiber back to the measuring device where it is detected and converted electronically to a concentration value of the particular species being monitored by the system.

Preferred polymers for use in the sensor or indicator of the invention are hydroxyethyl methacrylate homopolymer, polyvinyl alcohol and a copolymer of hydroxyethyl methacrylate with methyl methacrylate. Other polymers known in the art and containing the desired functionality discussed above may be used in the sensor or indicator of the invention, including polymers containing primary or secondary amine groups.

When the indicator or sensor is to be used for the determination of oxygen concentration, i.e. $pO_2$, the preferred fluorescent acid is 4-(1-pyrene)-butanoic acid (PBA) of the formula:

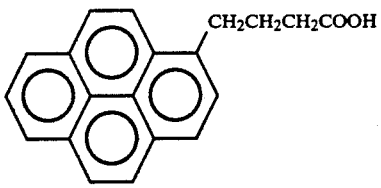

Other fluorescent pyrene derivatives that are responsive to the presence of oxygen may also be employed, for example, those that differ in the length, structure or position of the side group used for attachment to the polymer chain.

When the indicator or sensor is to be used for the determination of pH, the preferred fluorescent acid is 4-umbelliferonylacetic acid, also known as 4-(carboxymethyl)-umbelliferone (CMU), of the formula

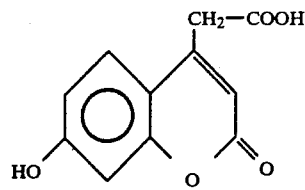

or the ethyl ester of CMU (CMUE) of the formula:

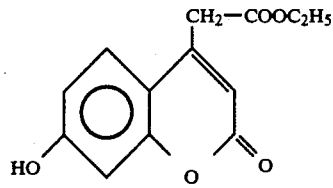

Other fluorescent umbelliferone derivatives that are responsive to pH may be used, for example those that differ in the length, structure or position of the side group through which attachment to the polymer chain is made.

A particularly preferred embodiment of the invention is a sensor which is adapted to determine both pH and $pO_2$ and such embodiment is a combination pH and $pO_2$ sensor wherein the above-described pendant hydroxyl groups are esterified in part with 4-umbelliferonylacetic acid and in part with 4-(1-pyrene)-butanoic acid.

The invention further provides a sensor adapted for carbon dioxide analysis which comprises an optical fiber having on the distal end thereof an adherent water-insoluble organic polymer esterified with 4-umbelliferonylacetic acid, said polymer being in contact with a bicarbonate electrolyte enveloped by a carbon dioxide-permeable, water impervious membrane mounted on the distal end of said fiber. The membrane preferably is composed of silicone rubber.

The fluorescent polymeric indicators according to the present invention offer substantial advantages toward optimal system fabrication in that they possess structural features that directly affect the performance of the sensor with respect to sensitivity, stability, response time and reversibility. Thus, the sensitivity of the system, i.e., the intensity of fluorescent light emitted in response to a given change in the condition being measured, is directly related to the concentration of indicating moieties in the polymer and to the access of analyte to these moieties. The concentration of indicating moieties is controllable, and may be directly optimized by known synthetic chemical procedures in which a selected proportion of free fluorescent indicator is bound to the base hydroxy-containing polymer via efficient esterification reactions. No change in chemical structure occurs in the fluorescence-generating portion of the indicator as a result of this procedure. If too high a concentration of indicator is attached, the sensor polymer becomes relatively hydrophobic which impairs access of the species being analyzed to the indicator leading to reduced sensitivity, slow response time, and poor reversibility. In addition undesired fluorescence interactions called "eximers" are promoted by high concentrations. If too low a concentration of indicator is attached, reduced sensitivity results. Consequently it is important to select the optimum indicator concentration as demonstrated below.

It is also important to select the optimum hydrophilicity of the polymer composition. This is accomplished according to the invention by selection of the hydrophilic to hydrophobic monomer ratio in the base polymer, and by selection of a curing agent and crosslink density as established by the ratio of curing agent to base polymer and the curing conditions such as temperature and time.

If the polymer has too low a hydrophilicity or water-swellability, the response of the sensor will be weak and slow; if the polymer swells too much, it becomes mechanically weak and difficult to retain on the optical fiber. Consequently it is important to achieve a satisfactory degree of swellability in the design of the polymer system. The satisfactory nature of the swellability and indicator level may be demonstrated empirically by the operation of the sensor, as disclosed herein.

DETAILED DESCRIPTION OF THE INVENTION

The invention will now be particularly described with reference to preferred embodiments of both the indicators and sensors incorporating such indicators. For the purpose of this description and to avoid duplication it is to be understood that similar considerations apply whether the indicator or the sensor is the specific embodiment under discussion. Further, it will be understood that the invention is not limited to the specific Examples disclosed.

In the preparation of a pH fluorescent indicator according to the invention, an umbelliferone analog, 4-(carboxymethyl)-umbelliferone (CMU) or its ethyl ester, (CMUE) was prepared and chemically attached to a polymer that contained hydroxyl groups by an esterification reaction. The resulting soluble fluorescent, pH-sensitive polymer was mixed with a crosslinking agent, coated onto a glass surface and cured into an insoluble, permanent form by heating.

For the preparation of an oxygen indicator a similar procedure is followed using PBA as the fluorescent indicator.

The following Examples illustrate the invention. Example 1 illustrates the preparation of starting materials.

EXAMPLE 1

(a) 4-(Carboxymethyl) umbelliferone (CMU)

CMU was prepared from resorcinol (1,3-dihydroxybenzene) and 3-ketoglutaric acid in a sulfuric acid medium.

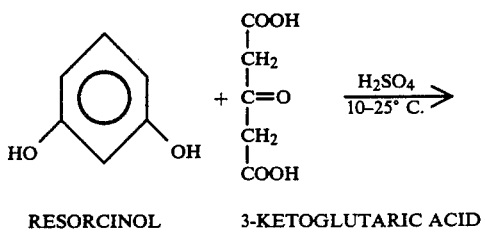

RESORCINOL     3-KETOGLUTARIC ACID

-continued

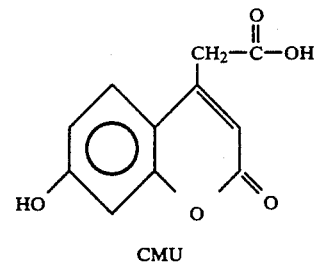

CMU 3-ketoglutaric acid was conveniently prepared from citric acid in a sulfuric acid medium:

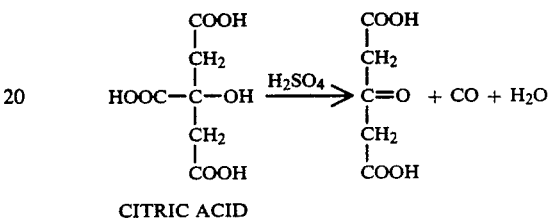

CITRIC ACID 192 g citric acid and 98% sulfuric acid (500 cc) were stirred for 1 hour in an ice bath, then heated in about one hour to 50°-55° C. and maintained at this temperature for 2 hours. At the end of this period the evolution of carbon monoxide had stopped. The reaction mixture was cooled to 10° C. in an ice bath and 110 g (1 mole) resorcinol was slowly added and the reaction left stirring overnight at room temperature. The reaction mixture was poured into 5 liters of ice-water to precipitate the solid product, CMU. The solid was recovered by filtration and washed several times with deionized water; the solid was redissolved in 2 liters of 5% sodium bicarbonate to neutralize residual sulfuric acid. The solution was washed 3 times in a separatory funnel with dichloromethane, discarding $CH_2Cl_2$ phase. The solution was filtered by vacuum to clarify. 100 ml of concentrated hydrochloric acid was slowly added to the solution to re-precipitate the solid product. The solid was then recrystallized twice from acetone-water (1:1) at 65°-70° C., and dried under vacuum at 50° C., giving pure CMU, in the form of fine white powder, melting point 200°-201° C. (uncorrected).

(b) 4-Carboxymethyl Umbelliferone Ethyl Ester (CMUE)

The ethyl ester of CMU was prepared by reacting CMU with ethanol in the presence of sulfuric acid.

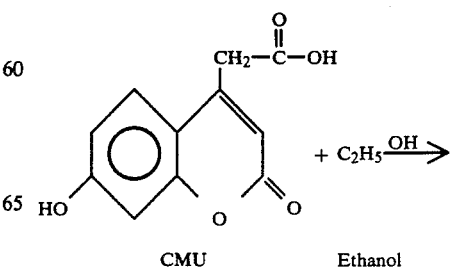

CMU        Ethanol

-continued

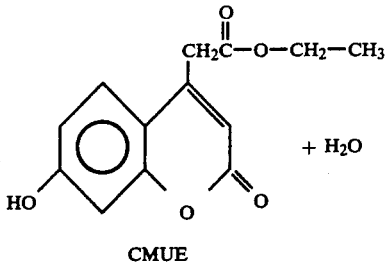

CMUE 10.0 g of CMU was dissolved in 100 cc ethanol at 60° C. 10 cc of 98% sulfuric acid was added and the solution stirred at 60° C. for 2 hours. The solution was poured into ice-water to precipitate the solid product. The solid was recovered by filtration, washed 3 times with 5% sodium bicarbonate solution (to neutralize sulfuric acid and remove residual unbelliferone-4-acetic acid), and dried under vacuum at 50° C. The solid was recrystallized twice from toluene-ethanol (1:1), decolorized with charcoal, and dried under vacuum at 50° C., giving pure umbelliferone-4-acetic acid ethyl ester in the form of fine white powder, melting point 156°–157° C. (uncorrected).

(c) Poly(HEMA-MMA) Copolymers

Copolymers of hydroxyethyl methacrylate (HEMA) and methyl methacrylate (MMA) were prepared by heating HEMA, MMA, and benzoyl peroxide (BPO) in tetrahydrofuran (THF) solution. The acrylic polymers were isolated by precipitation.

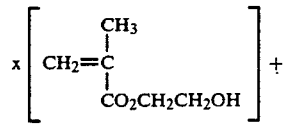

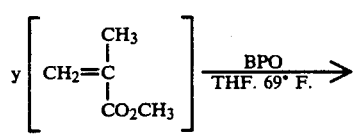

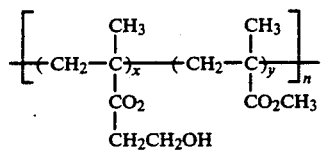

Copolymers of 3.4 parts HEMA and 1 part MMA (mole ratio of monomers 2.6:1); 4.5 parts HEMA and 1 part MMA (mole ratio of monomers 3.5:1); and 5.2 parts HEMA and 1 part MMA (mole ratio of monomers 4.0:1) were prepared.

(i) Poly(HEMA$_{2.6}$-MMA$_1$)

4.71 g methyl methacrylate, 15.96 g hydroxyethyl methacrylate, and 0.2 g benzoyl peroxide were placed in a 100 cc reaction kettle with 50 cc tetrahydrofuran under a nitrogen atmosphere. The mixture was stirred with an electric stirring motor for 5 hours, heating at 65°–68° C. The reaction mixture became opaque. 50 cc methanol was added to dissolve the reaction mixture and the solution became clear. The solution was poured into 250 ml of toluene with stirring, yielding a sticky mass of polymer. The toluene was decanted, and the polymer squashed to help remove solvent. The polymer was dried under vacuum and then shredded in a blender with 200 cc heptane, yielding small pieces. The heptane was removed by filtration and the polymer dried under vacuum, giving a white powder weight of 16.03 g (78% yield), of poly(HEMA-MMA) 2.6:1 mole ratio of monomers).

(ii) Poly(HEMA$_{3.5}$-MMA$_1$)

4.71 g methyl methacrylate, 21.28 g hydroxyethyl methacrylate and 0.2 g benzoyl peroxide were reacted and worked-up same as (i), giving a white powder weight of 21.3 g (82% yield) of poly(HEMA-MMA) (3.5:1 mole ratio of monomers).

(iii) Poly(HEMA$_{4.0}$-MMA$_1$)

25.03 g methyl methacrylate, 130.13 g hydroxyethyl methacrylate, and 1.30 g benzoyl peroxide were placed in a 1 liter reaction kettle with 300 cc tetrahydofuran. The mixture was stirred for 3 hours with an electric stirring motor, heating at 70°–75° C. The solution became viscous and opaque. 300 cc methanol was added to dissolve the reaction mixture and the solution became clear. The solution was poured into 2 liter of toluene with stirring, yielding a sticky mass of polymer. The toluene was decanted, and the polymer squashed to help remove solvent. The polymer was dried under vacuum and then shredded in a blender with 500 cc heptane, yielding small pieces. The heptane was decanted and the polymer dried under vacuum, giving a white powder weight of 104.4 g (67% yield), of poly(HEMA-MMA) (4.0:1 mole ratio of monomers).

EXAMPLE 2

The polymers prepared in Example 1(c) were tagged with the fluorescent indicators for pH and for pO$_2$ by esterification. The ratio of fluorescent indicators and polymer was selected such that there was 1 molecule of indicator for every 10 hydroxyl groups on the polymer, or one for every 100 hydroxyl groups. The polymer and indicator were dissolved in THF and an equivalent amount of dicyclohexylcarbodimide (DCC) added, using 1% 4-dimethylaminopyridine (DMAP) catalyst.

After the derivatized polymers were isolated and purified so as to eliminate unbound fluorescent compound, the actual amount of chemically bound fluorescent moiety was measured by ultraviolet-visible spectroscopy.

The preparation of pH sensing polymers with CMU is illustrated below:

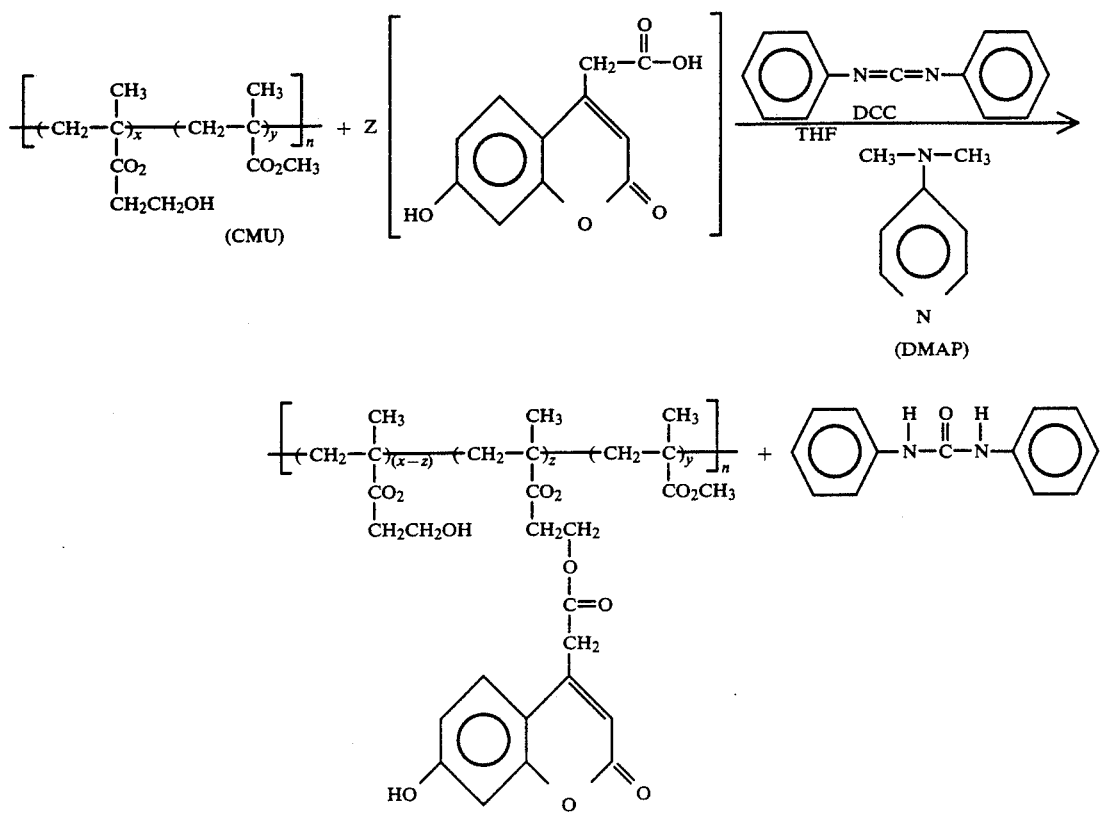

Umbelliferone-4-Acetic Acid Fluorescent Polymers a. Poly(HEMA-MMA) Base i. Poly(Hema$_{2.6}$-MMA$_1$)-9.7 Eq% CMU 4.5 g of poly(HEMA$_{2.6}$-MMA$_1$) was dissolved in 100 cc THF plus acetone (1:1) at boiling (60° C.). 0.571 g CMU was added and stirred until dissolved. 0.535 g dicyclohexylcarbodiimide, dissolved in 25 ml THF, and 6 mg dimethylaminopyridine, dissolved in 2 ml THF, was added and the solution was stirred for 2 hours at boiling (60° C.). The solution was diluted with 50 cc acetone and suction filtered to remove solid dicyclohexylurea. The solution was poured into 1 liter of 2.5% sodium bicarbonate solution with vigorous agitation to precipitate the polymer. The polymer was removed from the solution by filtration and washed with 2.5% sodium bicarbonate solution and 0.9% saline solution. The yellow-green mass of polymer was spread out into a thin layer and dried in a vacuum oven at 60° C. The polymer was then redissolved in 100 ml acetone-methanol (1:1), heating slightly to dissolve the polymer. The solution was again poured into 2.5% sodium bicarbonate solution to precipitate the polymer. This procedure was followed to remove residual CMU. The residual dye is soluble in the 2.5% bicarbonate solution. The polymer was collected, washed 3 times with 0.9% saline solution, spread into a thin layer, and dried under vacuum at 60° C., and crushed to powder with mortar and pestle. The powder was washed 5 times with 0.9% saline solution to remove residual sodium bicarbonate. The polymer was again dried under vacuum at 60° C., giving a lime-green powder, weight 4.17 g (83% yield) of poly(HEMA$_{2.6}$-MMA$_1$) with a theoretical molar substitution of 9.7% umbelliferone on HEMA monomer. Actual substitution was 7.4%.

ii. Poly(HEMA$_{3.5}$-MMA$_1$)-9.8 Eq% Umbelliferone-4-Acetic Acid 5.0 g of poly(HEMA$_{3.5}$-MMA$_1$) was dissolved in 100 cc THF plus acetone (1:1) at boiling (60° C.). 0.676 g umbelliferone-4-acetic acid was added and stirred until dissolved. 0.634 g dicyclohexyl carbodiimide, dissolved in 25 ml THF, and 6 mg dimethylaminopyridine, dissolved in 2 ml THF, were added and the solution stirred for 2 hours at boiling (60° C.). The reaction solution was then worked-up as described for i., giving a lime-green powder, weight 4.67 g (83% yield) of poly(HEMA$_{3.5}$-MMA$_1$) with a theoretical molar substitution of 9.8% umbelliferone on HEMA monomer. Actual substitution was 6.4%.

iii. Poly(HEMA$_{4.0}$-MMA$_1$)-0.96 Eq% CMU 20.0 g of poly(HEMA$_{4.0}$-MMA$_1$) was dissolved in 500 cc THF plus acetone (3:2) at boiling (60° C.). 0.271 g CMU was added and stirred until dissolved. 0.245 g dicyclohexylcarbodiimide and 25 mg dimethylaminopyridine, each dissolved in THF, were added and the solution stirred for 3 hours at boiling (60° C.). The reaction solution was then work-up as described for i., giving a limegreen powder, weight 13.81 g (69% yield) of poly(HEMA$_{4.0}$-MMA$_1$) with a theoretical molar substitution of 0.96% umbelliferone on HEMA monomer. Actual substitution was 0.53%.

EXAMPLE 3

Poly(vinyl alcohol)-0.96 Eq% CMUE

A fluorescent polymer based on poly(vinyl alcohol) (PVA) was prepared from a commercial PVA (88% hydrolyzed) and 1.0 equivalent-percent CMUE by ester interchange in dimethylacetamide solvent at elevated temperature.

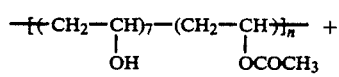

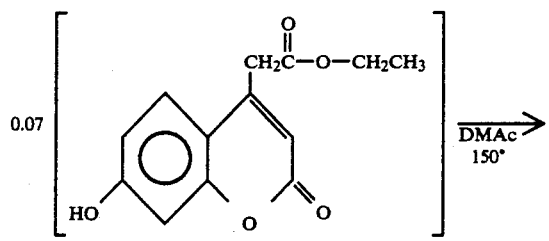

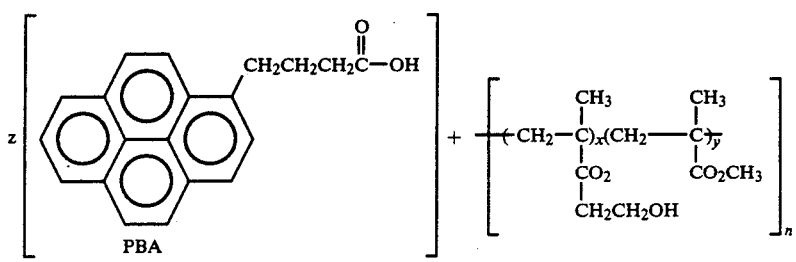

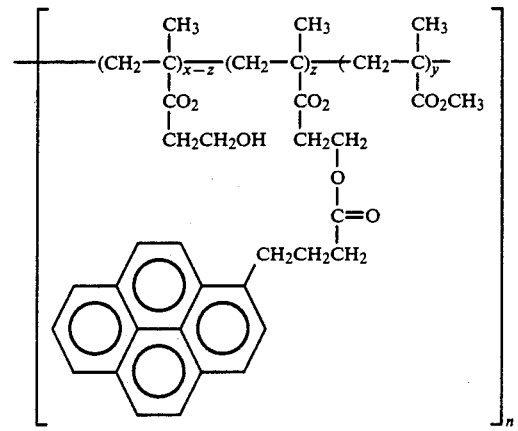

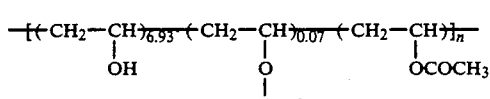

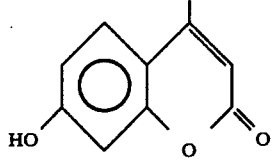

20.8 g of 88% hydrolyzed poly(vinyl alcohol) (Polyscience Cat. #4398) and 0.992 g CMUE were dissolved in 200 ml N,N-dimethylacetamide. 0.15 g of stannous octoate catalyst was added to the mixture. The solution gelled after stirring for ¼ hour at 100° C.; the gel was placed in an oven overnight at 100° C.; then dissolved in 250 ml deionized water. The solution was poured into 2.5 liter acetone, giving a white curd precipitate. The solid was recovered by filtration and centrifugation and washed 4 times with acetone to remove residual umbelliferone-4-acetic acid ethyl ester. The solid product was dried under vacuum at 50° C. and crushed to give a white powder, weight 17.23 g (80% yield) of poly(vinyl alcohol) with a theoretical molar substitution of 0.96% umbelliferone on the hydroxyl groups of the polymer. Actual substitution was 0.42%.

EXAMPLE 4

4-(Pyrene)-Butyric Acid Fluorescent Polymers

Oxygen-sensitive fluorescent polymers were prepared by routes analogous to those used for the pH sensitive polymers using PBA in place of CMU. Thus 10 equivalent-% PBA was esterified with 2.61:1 and 4:1 HEMA-MMA copolymers.

a. Poly(HEMA-MMA) Base i. Poly(HEMA$_{2.6}$-MMA$_1$)-9.7 Eq% 4-(1-Pyrene-Butyric Acid (PBA)

5.0 g of poly(HEMA$_{2.6}$-MMA$_1$) was dissolved in 100 ml THF acetone (1:1) at boiling (60° C.) 0.830 g of 4-(1-pyrene)-butyric acid was added and stirred until dissolved. 0.594 g dicyclohexylcarbodiimide, dissolved in 25 ml THF, and 6 mg dimethylaminopyridine, dissolved in 2 ml THF, were added and the solution stirred for 2 hours at boiling (60° C.). The solution was diluted with 50 cc acetone and suction filtered to remove the solids: the recovered solution was green in color. The solution was poured into 1 liter of 2.5% sodium bicarbonate solution of precipitate the polymer. The polymer was removed from the solution by filtration and washed with 2.5% sodium bicarbonate solution and 0.9% saline solution. The light green mass of polymer was spread out into a thin layer and dried in vacuum oven at 60° C. The polymer was then redissolved in 100 ml acetonemethanol (1:1), heating slightly to put into solution. The solution was suction filtered to remove residual PBA which is insoluble in these solvents. The solution was again poured into 2.5% sodium bicarbonate solution to precipitate the polymer. The polymer was collected, washed 3 times with 0.9% saline solution, spread into a thin layer, dried under vacuum at 60°

C., and crushed to powder with mortar and pestle. The powder was washed 5 times with 0.9% sodium chloride to remove residual sodium bicarbonate. The polymer was again dried under vacuum at 60° C., giving a light green powder, weight 3.07 g (53% yield) of poly(-HEMA$_{2.6}$-MMA$_1$) with a theoretical molar substitution of 9.7% PBA on HEMA monomer. Actual substitution was 9.5%.

ii. Poly(HEMA$_{3.5}$-MMA$_1$)-9.8 Eq% PBA 5.0 g of Poly(HEMA$_{3.5}$-MMA$_1$) was dissolved in 100 cc THF plus acetone (1:1) at boiling (60° C.). 0.890 g of PBA was added and stirred until dissolved. 0.634 g dicyclohexylcarbodiimide and 6 mg dimethylaminopyridine each dissolved in THF, were added and the solution stirred for 2 hours at boiling (60° C.). The reaction solution was then worked-up as described for i., giving a light green powder, weight 4.53 g (78% yield) of poly(HEMA$_{3.5}$-MMA$_1$) with a theoretical molar substitution of 9.8% PBA on HEMA monomer. Actual substitution was 9.3%.

iii. Poly(HEMA$_{4.0}$-MMA$_1$)-0.96 Eq% PBA 40.0 g of poly(HEMA$_{4.0}$-MMA$_1$) was dissolved in 800 cc THF plus acetone (1:1) at boiling (60° C.). 0.70 g of PBA was added and stirred until dissolved. 0.508 g dicyclohexylcarbodiimide and 50 mg dimethylaminopyridine, each dissolved in THF, were added and the solution stirred for 3 hours at boiling (60° C.). The reaction solution was then worked-up as described for i., giving a green powder, weight 29.63 g (73% yield) of poly(HEMA$_{4.0}$-MMA$_1$) with a theoretical molar substitution of 0.96% PBA on the HEMA monomer. Actual substitution was 0.78%.

EXAMPLE 5

Poly(vinyl alcohol)-0.96 Eq% PBA 20.8 g of 88% hydrolyzed poly(vinyl alcohol) and 1.153 g 4-(1-pyrene)-butyric acid were dissolved in 300 cc N,N-dimethylacetamide. 0.15 g of stannous octoate catalyst was added to the solution. The solution gelled after stirring for ½ hour at 100° C.; the gel was heated at 100° C. for 6 hours, then dissolved in 600 ml deionized water. The solution was suction filtered to remove residual PBA and poured into 2 liters acetone, giving a white curd precipitate. The solid was recovered by centrifugation; washed 2 times with acetone, and dried under vacuum, giving a brown, sticky mass. The polymer was then redissolved in 200 cc deionized water and precipitated in 500 cc acetone to dilute low volatile solvent, N,N-dimethylacetaminde. The polymer was dried under vacuum and shredded in a blender with 200 cc heptane, yielding small pieces. The heptane was decanted and the polymer dried under vacuum, giving a light green powder, weight 18.43 g (88% yield) of poly(vinyl alcohol) with a theoretical molar substitution of 0.96% PBA on the hydroxyl groups of the polymer. Actual substitution was 0.009%.

EXAMPLE 6

A polymer containing PBA plus CMU and 4:1 poly(-HEMA-MMA) was prepared. This combination polymeric indicator contains both acid and oxygen sensing moieties in a single molecule of polymer.

Poly(HEMA$_{4.0}$-MMA$_1$)-0.96 Eq% PBA and 0.96 Eq% CMU 15.27 g of poly(HEMA$_{4.0}$-MMA$_1$)-0.96% Eq% 4-(pyrene)-butyric acid was dissolved in 400 cc THF plus acetone (1:1) at boiling (60° C.). 0.203 g umbelliferone-4-acetic acid was added and stirred until dissolved. 0.190 g dicyclohexylcarbodiimide and 20 mg dimethylaminopyridine, each dissolved in THF, were added and the solution stirred for 3 hours at boiling (60° C.). The solution was suction filtered to remove solid dicyclohexylurea. The solution was poured into 2 liter of 2.5% sodium bicarbonate solution with vigorous agitation to precipitate the polymer. The polymer was removed from the solution and washed with 2.5% sodium bicarbonate solution and 0.9% saline solution. The yellowish mass of polymer was spread out into a thin layer and dried under vacuum. The polymer was shredded in a blender with 200 cc heptane, yielding granular powder. The heptane was decanted and the polymer washed with 2.5% sodium bicarbonate solution (to remove residual umbelliferone-4-acetic acid) and 0.9% saline solution (to remove residual sodium bicarbonate). The polymer was dried under vacuum, giving a yellowish powder, weight 13.98 g (90% yield) of poly(HEMA$_{4.0}$-MMA$_1$) with a theoretical molar substitution of 0.96% PBA and 0.96% umbelliferone on HEMA monomer. Actual substitution was 0.78% PBA and 0.2% CMU.

EXAMPLE 7

(a) Crosslinking (curing) of Fluorescent Polymers and Test of Adhesion To Glass

The fluorescent polymers prepared as described in Examples 2–6 were mixed with selected cross-linking agents and were coated onto glass plates and cured by heating to produce water-insoluble, adherent films that showed fluorescent responsiveness to pH or oxygen. The curing agents employed included poly(acrylic acid) (MW 2000), glutaraldehyde, tetraethylorthosilicate, gamma-glycidoxypropyltrimethoxysilane, and boric acid. All the curing agents operate by reaction with hydroxyl groups pendant from the polymers. The best results were obtained with the first two.

CROSS LINKED COATINGS

1. Procedure for Poly(Vinyl Alcohol) Fluorescent Polymer Insolubilization a. Glutaraldehyde Cross-linking 100 mg of poly(vinyl alcohol)-0.42% CMU polymer was dissolved in 4 ml deionized water and 1 ml ethanol. 40 mg glutaraldehyde, (50% in water), was added to the solution. Drops of the solution were placed onto glass surfaces and the films cured by heating at 100° C. for 1 hour.

b. Poly(Acrylic Acid) Cross-Linking 100 mg of poly(vinyl alcohol)-0.42% CMU polymer was dissolved in 5 ml deionized water. 30 mg of poly(acrylic acid) (65% in water, MW 2000) was added to the solution. Drops of the solution were placed onto glass surfaces and the films cured by heating at 100° C. for 1 hour.

(b) Testing of Insolubilized Poly(Vinyl Alcohol) Fluorescent Polymer Films in Water a. Still Water Glass plates with insolubilized films were placed in a beaker of still water for 6 days, and observed periodically for film stability, adhesion to glass and fluorescence.

b. Flowing Water

Glass plates with insolubilized films were placed in a beaker of stirring deionized water to create a flow environment. The glass plates were observed periodically for film stability, adhesion to glass, and fluorescence for 5 days.

Results of Water Immersion

PVA-CMU films crosslinked with polyacrylic acid or glutaraldehyde remained intact and fluorescent on the glass slides after being immersed in unstirred water for 164 hours. They also remained intact and fluorescent with little or no evidence of loss of polymer from the glass when immersed in stirred water for 123 hours. The films were still visibly adherent and there was no fluorescence in the surrounding water. For comparison, PVA fluorescent polymer cross-linked with other insolubilizers such as gamma-glycidoxypropyl trimethoxysilane or orthoboric acid showed substantial loss of polymer content and fluorescence from the glass slides within 24 hours, the films visibly detaching and floating off.

(c) Analyses

1. Nuclear Magnetic Resonance Spectra (NMR);

Analysis for H'NMR was performed on the fluorescent indicators and polymers using a Varian XL-300 spectrometer at a solution concentration of 30–50 mg compound/0.5 cc dimethylsulfoxide-d6.

Proton spectra (HNMR) were consistent with the structures 4-(carboxymethyl)umbelliferone (CMU) and 4-(carbethoxymethyl)umbelliferone (CMUE)

Elemental analyses for carbon and hydrogen of the synthesized compounds CMU and CMUE are in agreement with theoretical expectations. The results are shown below:

| CMU | THEORY (%) | RESULTS (%) |
|---|---|---|
| C | 60.00 | 60.00 |
| H | 3.63 | 3.60 |
| N | 0.00 | 0.00 |
| CMUE | THEORY (%) | RESULTS (%) |
| C | 62.90 | 62.91 |
| H | 4.84 | 4.88 |
| N | 0.00 | 0.00 |

4. UV Measurements

While given amounts of fluorescent indicator were mixed with the support polymers in order to react them together, it cannot be assumed that all indicator was successfully bound to the polymer during the synthetic reaction. The actual amount of fluorescent indicator attached to a polymer was determined using ultraviolet spectral measurements.

a. Sample Preparations i. Umbelliferone-4-Acetic Acid Ethyl Ester (CMUE)

100 mg of umbelliferone-4-acetic acid ethyl ester was dissolved in 100 cc methanol plus THF (1:1) or N,N-

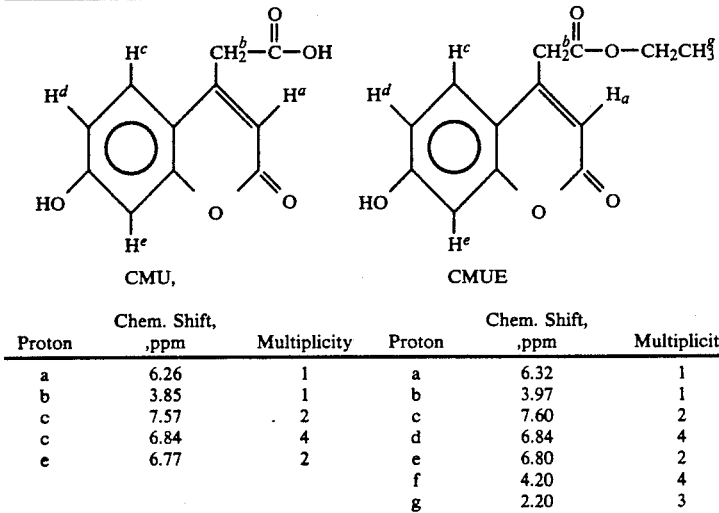

| Proton | Chem. Shift, ppm | Multiplicity | Proton | Chem. Shift, ppm | Multiplicity |
|---|---|---|---|---|---|
| a | 6.26 | 1 | a | 6.32 | 1 |
| b | 3.85 | 1 | b | 3.97 | 1 |
| c | 7.57 | 2 | c | 7.60 | 2 |
| c | 6.84 | 4 | d | 6.84 | 4 |
| e | 6.77 | 2 | e | 6.80 | 2 |
|   |   |   | f | 4.20 | 4 |
|   |   |   | g | 2.20 | 3 |

The $^{13}C$ NMR spectrum of CMUE was also consistent with the expected structure, 2. Infrared Spectra Analysis was performed using an Analect Instruments FX6250 Fourier Transform Infrared Spectrometer. Transmission spectra was obtained on samples prepared either by casting a film onto a salt plate from methanol plus THF solution, typically, or by nujol mull with paraffin oil. A background spectrum was first obtained and algebraic subtraction was automatically performed, giving a spectrum of the sample alone.

Infrared (Fourier Transform) spectra of the polymers were consistent with expected structures, showing hydroxyl and carboxyl in complex spectra.

3. Elemental Analysis

C, H, and N analysis was performed on umbelliferone-4-acetic acid and umbelliferone-4-acetic acid ethyl ester by combustion.

dimethylacetamide, heating slightly to dissolve the compound. The solution was then diluted to give a final concentration of 0.005 mg compound/cc solvent.

ii. 4-(Pyrene)-Butyric Acid (PBA)

(Same as a.i.).

iii. Poly(HEMA-MMA) - Fluorescence Polymers

The polymer was dissolved in methanol plus THF (1:1) at a solution concentration of 0.025–0.50 mg polymer/cc solvent.

iv. Poly(Vinyl Alcohol) - Fluorescence Polymers

The polymer was dissolved in N,N-dimethylacetamide at a solution concentration of 2.3 mg polymer/cc solvent.

b. Analytical Procedure

A Cary 14 Recording Spectrophotometer was used to scan the solution samples in the UV/vis wavelength range of 400–250 A. The solution solvent, common for both the fluorescent dye alone and as attached to the polymer base, was scanned first to determine the baseline. The fluorescent dye solution was then scanned, followed by the fluorescent polymer solution.

The content of fluorescent species in the polymer was determined by comparing the intensities of the spectra of the polymer and of the unattached fluorescent compounds.

The results were as follows:

| POLYMER | FLUORESCENT INDICATOR | REACTANTS, MOLE RATIO: [FLUORESCER] [HYDROXYL] (CALC'D) | PRODUCT, MOLE RATIO: [FLUORESCER] [HYDROXY]. (FOUND BY UV) |
|---|---|---|---|
| Poly($HEMA_{2.6}$-$MMA_1$) | CMU | $9.7 \times 10^{-2}$ | $7.4 \times 10^{-2}$ |
| Poly($HEMA_{3.5}$-$MMA_1$) | CMU | $9.8 \times 10^{-2}$ | $6.4 \times 10^{-2}$ |
| Poly($HEMA_{4.0}$-$MMA_1$) | CMU | $9.6 \times 10^{-3}$ | $5.3 \times 10^{-3}$ |
| Poly(vinyl alcohol) | CMU | $9.6 \times 10^{-3}$ | $4.2 \times 10^{-4}$ |
| Poly($HEMA_{2.6}$-$MMA_1$) | PBA | $9.7 \times 10^{-2}$ | $9.5 \times 10^{-2}$ |
| Poly($HEMA_{3.5}$-$MMA_1$) | PBA | $9.8 \times 10^{-2}$ | $9.3 \times 10^{-2}$ |
| Poly($HEMA_{4.0}$-$MMA_1$) | PBA | $9.6 \times 10^{-3}$ | $7.8 \times 10^{-3}$ |
| Poly(vinyl alcohol) | PBA | $9.6 \times 10^{-3}$ | $9.1 \times 10^{-5}$ |
| Poly($HEMA_{4.0}$-$MMA_1$) | CMU | $9.6 \times 10^{-3}$ | $2.0 \times 10^{-3}$ |
|  | PBA | $9.7 \times 10^{-3}$ | $7.8 \times 10^{-3}$ |

(d) Fluorescence Measurements

1. Umbelliferone Fluorescent Polymers

The fluorescence excitation spectra of the polymer-linked umbelliferone indicators demonstrated pH response that paralleled the fluorescent indicator alone.

2. Pyrene Butyric Acid Fluorescent Polymers

The fluorescence emission spectra of the polymer-linked pyrene acid indicators demonstrate $O_2$ response that paralleled the fluorescent indicator alone. The indicator solutions were treated by bubbling the gas indicated in the table into the solution in order to elicit the response.

a. Sample Preparations i. 4-Methyl Umbelliferone 2.0 g of 4-methyl umbelliferone (Aldrich Chemicals, Lot 12872-4) was mixed for 5 minutes in 10 ml $H_2O$; small amounts of umbelliferone go into solution. The solution was recovered by filtration, giving an unknown concentration of umbelliferone in solution. 1 cc of this solution was added to 9.0 cc of aqueous buffer solutions, giving final pH's: 6.60, 7.10, 7.40, 7.82, 9.60.

ii. Umbelliferone-4-Acetic Acid Ethyl Ester (CMUE)

2.0 g of umbelliferone-4-acetic acid ethyl ester was mixed for 5 minutes in 10 ml $H_2O$: small amounts of the umbelliferone go into solution. The solution was recovered by filtration, giving an unknown concentration of umbelliferone ester in solution. 1 cc of this solution was added to 9.1 ml of buffer solutions, giving final pH's: 5.20, 6.60, 7.10, 7.40, 7.80, 9.60.

iii. 4-(Pyrene)-Butyric Acid (PBA)

0.10 g PBA was mixed for 5 minutes in 10 ml of 2.5% sodium bicarbonate solution; small amounts of PBA go into solution. The solution was recovered by filtration, giving an unknown concentration of PBA in solution. 1 cc of this solution was added to 9.0 ml of pH=7.40 buffer solution.

iv. Poly(HEMA-MMA) - Fluorescence Polymers

The polymer was dissolved in methanol plus THF (1:1) at a solution concentration of 0.05–0.25 mg polymer/cc solvent. The solution was dropped onto a glass slide, cut to fit diagonally in a spectrophotometer quartz cell, and dried in oven (50° C.) to cast a film.

v. Poly(Vinyl Alcohol) - Fluorescence Polymers

The polymer was dissolved in deionized water at a solution concentration of 2.3 mg polymer/cc solvent.

Glutaraldehyde, 50% in water, was added to the solution as a crosslinking agent at 20 weight % glutaraldehyde to polymer. The solution was dropped onto a glass slide cut to fit diagonally in a spectrophotometer quartz cell, and the films were cured by heating at 100° C. for 1 hour.

b. Analytical Procedure

A Perkin-Elmer LS-5 Fluorescence Spectrophotometer was used with Perkin-Elmer K100 Recorder. Typical settings used: 10 nm/cm recorder speed, 120 nm/min scan speed, response @ 1, emission slit @ 10 nm, and excitation slit @ 10 nm.

i. pH Response: The glass slide with polymer film was placed in a quartz cell in a buffered pH solution. An excitation scan was performed at a wavelength range of 250–450 nm with a constant emission wavelength of 460 nm, typically. An auto concentration setting of 90.00 was used, i.e. a prescan of the excitation range automatically placed the highest peak at 90% full scale. A change in pH was obtained by placing the glass slide with polymer film in a different buffered pH solution. An analogous procedure was followed for a solution of a compound or polymer.

ii. $O_2$ Response: The glass slide with polymer film was placed in a quartz cell in a buffered pH=7.40 solution. An emission scan was performed at a wavelength range of 350–550 nm with a constant excitation wavelength of 332 nm, typically. A "fix scale" setting was used, i.e., a setting of 1.0 or 2.0, typically, was used to obtain a desired height on the recorder chart. A change of $O_2$ concentration was obtained by bubbling an inert gas (nitrogen or helium) to decrease $O_2$ concentration, or air, to increase $O_2$ concentration, through the aqueous buffer solution. An analogous procedure was followed for a solution of a compound or polymer.

The results were as follows:

| 1. Umbelliferone Fluorescent Polymers | | | |
|---|---|---|---|
| 4-Methyl Umbelliferone In Aqueous Solution | | CMUE In Aqueous Solution | |
| pH | I332/I375 | pH | I325/I380 |
| 6.60 | 3.18 | 5.20 | 30.00 |
| 7.10 | 1.18 | 6.60 | 4.50 |
| 7.40 | 0.84 | 7.10 | 2.20 |
| 7.82 | 0.67 | 7.40 | 1.50 |
| 9.60 | 0.66 | 7.80 | 0.90 |
|  |  | 9.60 | 0.50 |
| Poly($HEMA_{2.6}$-$MMA_1$) -7.4 Eq % CMU. Cast Film | | Poly($HEMA_{3.5}$-$MMA_1$) -6.4 EQ % CMU. Cast Film | |
| pH | I335/I380 | pH | I330/I380 |

| 5.20 | 25.43 | 5.20 | 4.80 |
| 7.40 | 2.92 | 7.40 | 1.30 |
| 9.60 | 1.83 | 9.60 | 1.20 |

| Poly(HEMA$_{4.0}$-MMA$_1$) -0.53 Eq % CMU. Cast Film | | Poly(vinyl alcohol-0.042 Eq % CMU. Cast Film with Glutaraldehyde | |
|---|---|---|---|
| pH | I332/I375 | pH | I330/I385 |
| 5.20 | 25.0 | 6.30 | 2.32 |
| 7.40 | 1.58 | 7.40 | 1.15 |
| 8.30 | 1.23 | 8.30 | 0.55 |
| 9.00 | 0.61 | 9.00 | 0.42 |

2. Pyrene Butyric Acid Fluorescent Polymers PBA In Aqueous Solution

| Treatment | ΔI376 (I initial = 80%) |
|---|---|
| He: 3 min. | +21 |
| Air: 1 min. | −21 |
| He: 1 min. | +20 |
| Air: 5 sec. | −11 |
| Air: 5 sec. | −08 |
| He: 3 sec. | +07 |
| He: 3 sec. | +05 |

I = Light intensity at wavelength (nm) given.
ΔI = Change in fluorescence intensity, units of percent of full scale chart amplitude at 376 nm.

Poly(HEMA$_{2.6}$-MMA$_1$)- 9.5 Eq% PBA Cast Film

The polymer was dissolved in solvent (methanolacetone) at a concentration of 1 mg polymer/cc solvent and emission scans were done on this solution. The peaks at 397 nm and 376 nm were very responsive to changes in gas (O$_2$); bubbling of helium for only short periods of time increased the peak heights substantially and reintroduction of air decreased the peak heights. The solution concentration was then decreased to 0.1 mg polymer/cc solvent and this solution cast a film on glass. When emission scans were done and oxygen concentration in the solution was varied as above, the major peak observed was a broad peak at 480 nm, nonresponse to gases. This peak was determined to be due to eximer fluorescence interaction (transient dimerization-complexation) by the PBA indicator. It was concentration dependent, i.e. when the solution concentration from which the film was cast was decreased, it led to reduction or disappearance of the 480 nm emission. The solution concentration was decreased to 0.01 mg polymer/cc solvent, a film was cast on a glass slide, and emission scans at varying O$_2$ concentration were repeated. Although a spectrum broadening was observed, the major emission peaks were at 395 nm and 378 nm and not at the eximer fluorescence at 480 nm. The peaks at 395 and 378 nm were very responsive to changes in O$_2$.

| pO$_2$ | ΔI378 |
|---|---|
| He: 30 sec. | +32 |
| Air: 15 sec. | −30 |
| He: 5 sec. | +35 |

| Poly(HEMA$_{3.5}$-MMA$_1$) - 9.3 Eq % PBA Cast Film | |
|---|---|
| pO$_2$ | ΔI395 |
| He: 1 sec. | +28 |
| Air: 5 sec. | −38 |
| Air: 1 sec. | −6 |

| Poly(HEMA$_{4.0}$-MMA$_1$) - 0.78 Eq % PBA Cast Film | |
|---|---|
| pO$_2$ | ΔI395 |
| N$_2$: 30 sec. | +22 |
| Air: 1 sec | −55 |
| N$_2$: 5 sec. | +20 |
| Air: 1 sec. | −11 |

| Poly(vinyl alcohol) - 9.1 × 10$^{-3}$ Eq % PBA Cast Film With Glutaraldehyde (20%) | |
|---|---|
| pO$_2$ | ΔI378 |
| N$_2$: 5 sec. | +28 |
| Air: 3 sec. | −37 |
| N$_2$: 1 sec. | +4 |
| Air: 1 sec. | −8 |

3. POLY(HEMA$_{4.0}$-MMA$_1$) - 0.78 Eq% PBA+0.20 Eq% CMU

The polymer with both fluorescent indicators attached allowed both pH and pO$_2$ measurement with a single polymeric film coating. The fluoresence excitation spectra of the polymer-linked unbelliferone demonstrated excellent response to changes in pH.

| pH | I325/I345 |
|---|---|
| 5.20 | 1.51 |
| 7.40 | 0.94 |
| 8.30 | 0.63 |

In addition, the fluorescence emission spectra of polymer-linked PBA demonstrated excellent response to changes in O$_2$ concentration.

| pO$_2$ | ΔI395 |
|---|---|
| N$_2$: 15 sec. | +22 |
| Air: 1 sec. | −26 |

Additional spectra were obtained from this fluorescent polymer, further demonstrating excellent response to both changing pH and O$_2$ concentration with a single bifunctional polymer coating.

EXAMPLE 8

This Example illustrates the preparation and use of optical fiber sensors incorporating the fluorescent polymers of the invention.

A. Optical Fiber Preparation:

A 400 μm fused silica optical fiber was cleaved and the tip polished with 15, 8, 5 and 3 μm polishing paper. Approximately 1 mm of fiber tip was soaked in silicone stripping solution for approximately 5 minutes to remove silicone cladding covering the glass core. The exposed glass was then washed in mild detergent and rinsed in water to remove excess cladding or stripping solution.

B. Surface Preparation

Surface bonding or curing agents can be employed to enhance polymer adhesion to the optical fiber surface. The agents act by forming a bridge between the polymer and the glass surface.

Gamma-glycidoxypropyltrimethoxysilane, mentioned as a typical curing agent in Example 7, has the formula:

and is a species within a group of compounds of the general formula R—Si(OCH$_3$)$_3$, wherein R is an organic group which reacts with the polymer and is chosen according to the characteristics of the particular polymer to be bonded to glass. For example, gamma-glycidoxypropyltrimethoxysilane is particularly suitable for bonding PMMA:PHEMA and PVA polymers to optical glass fibers.

The sensor output was analyzed as follows:
1. Ratio of emission intensity produced by two distinct polychromatic excitation wavelength ranges, typically 5-15 nm at half peak height around a central wavelength. The change in this ratio was then correlated to either oxygen, carbon dioxide or hydrogen ion

| Silane Compound | Formula | Bonding polymer |
|---|---|---|
| 1. N-($\beta$-aminoethyl)-$\gamma$-amino propyltrimethoxy silane | $NH(CH_2)_2NH$ — $CH_2$ — $(CH_2)_2Si(OCH_3)_3$ | a. PMMA:PHEMA<br>b. PVA |
| 2. $\gamma$-methacryloxy propyl-trimethoxy silane | $CH_2=C(CH_3)-C(O)-O(CH_2)_3Si(OCH_3)$ | a. PMMA:PHEMA<br>b. PVA |
| 3. N-2-(vinylbenzylamino)-ethyl-3-amino propyltrimethoxy silane | $CH_2=CH-C_6H_4-CH_2NH(CH_2)_2NH(CH_2)_3Si(OCH_3)_3$ | PMMA:PHEMA |

The above agents were utilized in one of two ways:
1. A 0.25 to 1.5% solution of the silane bonding gent was prepared in water, allowing about 20 minutes for hydrolysis to take place. The glass surface to which the polymer is to be bonded is dipped in the silane solution and gently agitated for 1-2 minutes. The silane-coated glass surface is then heated in an oven at a temperature of 105° C. for 30-40 minutes.
2. 1 to 2% by weight of the silane was added directly to a solution of the fluorescent polymer. The glass surface was then dipped directly into the solution and dried under heat.

Of desired, silane adhesion maybe improved by adding a mild acid to the solution, adjusting to a pH 3-4.

Preparation of Sensors 1. pH Sensors

Optical fibers prepared as described in A above and treated with silane bonding agent as described in B above were bonded to pH-sensitive fluorescent polymers.

Approximately 0.02 ml of the fluorescent polymer was applied to the fiber tip either by dipping or applying with a microliter syringe. The resulting optical sensor was then heated in an oven at a temperature of 80°-100° C. for approximately one hour. After drying, the finished sensor is soaked in dilute sodium bicarbonate solution to hydrate the polymer.

2. pCO$_2$ Sensor:

A pH sensor was constructed using the pH sensitive fluorescent polymer of Examples 2-3. The sensor was then soaked in electrolyte solution containing approximately 2 mM sodium bicarbonate for 1-2 hours. The sensor was then dipped in liquid silicone giving a 5-10 mil membrane thickness.

3. pO$_2$ Sensor:

The construction was analogous to pH sensor construction, but using an oxygen-sensitive fluorescent polymer as described in Example 4 or 5 in place of the pH-sensitive polymer.

Fluorescence measurements for each of the above sensors were made using a modified Perkin-Elmer LS5 spectrofluorimeter. Excitation and emission wavelengths were scanned over preset ranges, producing complete spectra for each sensor. In addition, emission intensity versus time was monitored.

concentration.

2. Measurement of the polychromatic emission intensity over a designated frequency range, typically 80-100 nm. The emission intensity or the area of the emission spectrum was then correlated to oxygen, carbon dioxide, or hydrogen ion concentration.

Calibration curves were generated for all three sensors using both schemes.

The fluorescence measurements confirmed that there are no significant differences between the free indicator and the polymer bound indicator in each case.

The results of the above experiments established that, in accordance with the invention, fluorescent indicators have been successfully bonded to polymers and the resultant fluorescent polymers have strength, adhesion to surfaces, permeability to water, and can be coated on and permanently bonded to the distal end of optical fibers, thereby providing durable fluorescent sensors for pH and oxygen, as well as combination pH and pO$_2$ and, where appropriate, pCO$_2$. Moreover, said fluorescent sensors are characterized by rapid response and ease of calibration and may be used in a conventional light-analysing apparatus.

We claim:

1. A sensor for the determination of the concentration of a dissolved substance in an aqueous medium comprising an optical fiber having a distal end to which is stably bonded an adherent, water-insoluble, stable, rapid response fluorescent polymeric indicator comprising an organic polymeric portion to which is covalently bonded, through ester or amide linkages, a plurality of fluorescent organic substituents, which may be the same or different, said polymeric portion being derived from an organic polymer having functionality consisting of hydroxyl or amine groups depending from the polymer chain and said fluorescent organic substituents being derived from fluorescent indicator molecules having, in addition to the desired fluorescent and indicating properties, linking functionality suitable for forming ester or amide linkages with said polymer functionality, said linking functionality being located sufficiently remote from the fluorescent portion of the indicator molecules so that it does not adversely affect the fluorescent indicating capability of the indicator molecule when the said amide or ester linkages are formed.

2. A sensor according to claim 1, wherein said polymer contains pendant hydroxyl groups, a proportion of said groups being esterified with one or more fluorescent organic carboxylic acids.

3. A sensor according to claim 2, wherein said polymer is a hydroxyethyl methacrylate polymer.

4. A sensor according to claim 3 wherein said polymer is a copolymer with methyl methacrylate.

5. A sensor according to claim 2, wherein said polymer is poly(vinyl alcohol).

6. An oxygen sensor according to claim 2 wherein said fluorescent acid is 4-(1-pyrene)-butanoic acid.

7. A pH-sensor according to claim 2 wherein said fluorescent acid is 4-umbelliferonylacetic acid.

8. A sensor according to claim 7 adapted for carbon dioxide analysis wherein said fluorescent polymer is in contact with a bicarbonate electrolyte enveloped by a carbon-dioxide-permeable, water-impervious membrane mounted on the distal end of said fiber.

9. A sensor according to claim 8, wherein said membrane is composed of silicone rubber.

10. A combination pH and $pO_2$ sensor according to claim 2, wherein said pendant hydroxyl groups are esterified in part with 4-umbelliferonylacetic acid and in part with 4-(1-pyrene)butanoic acid.

11. A sensor according to claim 2, wherein said polymer is bonded to said fiber distal end with a curing agent reactive with said pendant hydroxyl groups.

12. A sensor according to claim 10, wherein said curing agent is polyacrylic acid, glutaraldehyde, tetraethyl orthosilicate, gamma-glycidoxypropyltrimethoxysilane or boric acid.

13. A stable, rapid response fluorescent polymeric indicator for the determination of the concentration of a dissolved substance in an aqueous medium, said indicator comprising an organic polymeric portion to which is covalently bonded, through ester or amide linkages, a plurality of fluorescent organic substituents, which may be the same or different, said polymeric portion being derived from an organic polymer having functionality consisting of hydroxyl or amine groups, depending from the polymer chain and said fluorescent organic substituents being derived from fluorescent indicator molecules having, in addition to the desired fluorescent and indicating properties, linking functionality suitable for forming ester or amide linkages with said polymer functionality, said linking functionality being located sufficiently remote from the fluorescent portion of the indicator molecule so that it does not adversely affect the fluorescent indicating capability of the indicator molecule when the said amide or ester linkages are formed.

14. An indicator according to claim 13, wherein said polymer contains pendant hydroxyl groups, a proportion of said groups being esterified with one or more fluorescent organic carboxylic acids.

15. An indicator according to claim 14, wherein said polymer is poly(vinyl alcohol).

16. An indicator according to claim 14, wherein said polymer is a hydroxyethyl methacrylate polymer.

17. An indicator according to claim 16, wherein said polymer is a copolymer with methyl methacrylate.

18. An oxygen indicator according to claim 14, wherein said carboxylic acid is 4-(1-pyrene)-butanoic acid.

19. A pH indicator according to claim 14, wherein said carboxylic acid is 4-umbelliferonylacetic acid.

20. A combination pH and $pO_2$ indicator according to claim 14, wherein said carboxylic acids, are, respectively, 4-umbelliferonylacetic acid and 4-(1-pyrene)-butanoic acid.

* * * * *